United States Patent
Haartsen

(10) Patent No.: US 10,772,517 B2
(45) Date of Patent: Sep. 15, 2020

(54) DUAL-EAR HEART RATE DETECTION USING ASYMMETRY

(71) Applicant: Plantronics, Inc., Santa Cruz, CA (US)

(72) Inventor: Jacobus Cornelis Haartsen, Rolde (NL)

(73) Assignee: Plantronics, Inc., Santa Cruz, CA (US)

(*) Notice: Subject to any disclaimer, the term of this patent is extended or adjusted under 35 U.S.C. 154(b) by 406 days.

(21) Appl. No.: 15/662,131

(22) Filed: Jul. 27, 2017

(65) Prior Publication Data
US 2019/0029529 A1 Jan. 31, 2019

(51) Int. Cl.
*A61B 5/02* (2006.01)
*A61B 5/024* (2006.01)
(Continued)

(52) U.S. Cl.
CPC .......... *A61B 5/024* (2013.01); *A61B 5/02427* (2013.01); *A61B 5/02438* (2013.01); *A61B 5/02444* (2013.01); *A61B 5/6803* (2013.01); *A61B 5/6815* (2013.01); *A61B 5/721* (2013.01); *H04R 5/033* (2013.01); *A61B 2560/0233* (2013.01); *A61B 2560/0406* (2013.01); *A61B 2562/02* (2013.01); *A61B 2562/0238* (2013.01); *H04R 1/1041* (2013.01); *H04R 5/0335* (2013.01); *H04R 2420/07* (2013.01)

(58) Field of Classification Search
CPC ... A61B 5/024; A61B 5/6803; A61B 5/02427; A61B 5/6815; A61B 5/721; A61B 5/02444; A61B 2/02438; A61B 2560/0406; A61B 2560/0233; A61B 2562/0238; A61B 2562/02; H04R 5/033; H04R 2420/07; H04R 1/1041; H04R 5/0335
See application file for complete search history.

(56) References Cited

U.S. PATENT DOCUMENTS

2013/0131519 A1* 5/2013 LeBoeuf .............. A61B 5/0077
  600/476
2015/0351688 A1* 12/2015 Just ........................ A61B 5/681
  600/407
2018/0310847 A1* 11/2018 Ornato ............... A61B 5/02427

OTHER PUBLICATIONS

Tomita, Yohei. "Asynchronous noise removal for earbud-based PPG sensors." 2016 38th Annual International Conference of the IEEE Engineering in Medicine and Biology Society (EMBC). IEEE, 2016 (Year: 2016).*

(Continued)

*Primary Examiner* — Navin Natnithithadha
*Assistant Examiner* — Andrey Shostak
(74) *Attorney, Agent, or Firm* — Chuang Intellectual Property Law

(57) ABSTRACT

Methods and apparatuses for heart rate detection are described. In one example, a headphones apparatus and method includes emitting a first light in a first light direction directed at a left ear location from a left ear light emitter, and detecting a detected first light at a left ear light detector following interaction of the first light with a left ear tissue. The method includes emitting a second light in a second light direction directed at a right ear location from a right ear light emitter, the right ear location different from the left ear location. The method further includes detecting a detected second light at a right ear light detector following interaction of the second light with a right ear tissue, and estimating a heart rate from the detected first light and the detected second light.

17 Claims, 15 Drawing Sheets

(51) Int. Cl.
*A61B 5/00* (2006.01)
*H04R 5/033* (2006.01)
*H04R 1/10* (2006.01)

(56) References Cited

OTHER PUBLICATIONS

Tomita, "Asynchronous noise removal for earbud-based PPG sensors," in Engineering in Medicine and Biology Society (EMBC), 2016 IEEE 38th Annual International Conference, 2016, pp. 259-262.

* cited by examiner

DUAL-EAR HEART RATE DETECTION USING ASYMMETRY

BACKGROUND OF THE INVENTION

Many heart rate sensors, both in clinical and in consumer applications, use the optical photoplethysmographic (PPG) method to extract the heart rate (HR) from the human body. The PPG method is based on the modulation of light parameters (reflection and/or absorption) when interacting with a blood vessel. Most clinical methods use light transmission through the finger. In consumer applications, the reflective method is typically used, for example by using PPG sensors in wristbands, watches, or cuffs worn at the upper arm. However, relative to chest strap monitors, PPG sensors typically suffer from reduced accuracy. As a result, improved methods and apparatuses for heart rate detection using PPG sensors are needed.

BRIEF DESCRIPTION OF THE DRAWINGS

The present invention will be readily understood by the following detailed description in conjunction with the accompanying drawings, wherein like reference numerals designate like structural elements.

DESCRIPTION OF SPECIFIC EMBODIMENTS

Methods and apparatuses for heart rate detection are disclosed. The following description is presented to enable any person skilled in the art to make and use the invention. Descriptions of specific embodiments and applications are provided only as examples and various modifications will be readily apparent to those skilled in the art. The general principles defined herein may be applied to other embodiments and applications without departing from the spirit and scope of the invention. Thus, the present invention is to be accorded the widest scope encompassing numerous alternatives, modifications and equivalents consistent with the principles and features disclosed herein.

Block diagrams of example systems are illustrated and described for purposes of explanation. The functionality that is described as being performed by a single system component may be performed by multiple components. Similarly, a single component may be configured to perform functionality that is described as being performed by multiple components. For purpose of clarity, details relating to technical material that is known in the technical fields related to the invention have not been described in detail so as not to unnecessarily obscure the present invention. It is to be understood that various example: of the invention, although different, are not necessarily mutually exclusive. Thus, a particular feature, characteristic, or structure described in one example embodiment may be included within other embodiments unless otherwise noted.

Figure 17:
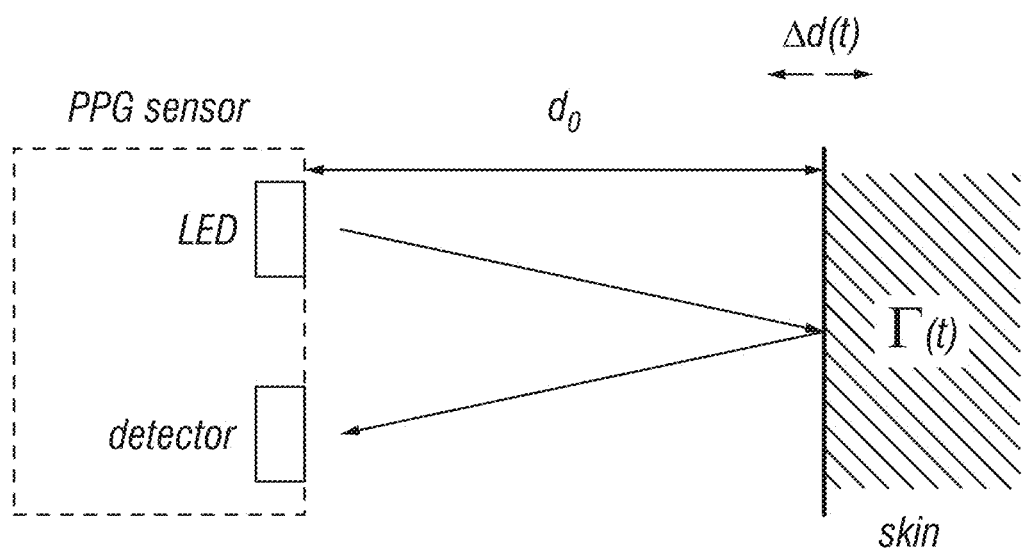
FIG. 17 illustrates operation of a PPG sensor in one example.

The inventor has recognized certain limitations in current methods and apparatuses extracting (also referred to herein as estimating, detecting, or determining) user heart rate utilizing PPG sensors. One major cause of interference in the PGG measurement is movement, also indicated as motion artifact (MA). The PPG measurement is based on light sent by a light source (e.g., a light emitting diode (LED)), reflected by blood vessels in the skin, and detected by a photo detector. FIG. 17 illustrates operation of a PPG sensor in one example. The problem is the propagation distance do between sensor and the reflective medium. The light intensity depends on the propagation distance $d_0$: when e.g. due to movement, the propagation distance changes (represented by the time varying parameter $\Delta d$), the light is modulated and this can severely interfere with the modulation caused by the light reflection/absorption (represented by the time varying reflection coefficient $\Gamma$) which is representative for the heart rate.

If the distance do is reduced to zero (the sensor makes contact to the skin), much of the motion artifact effects are gone, but still some effects due to movement are left. This is a result of (1) the distance left between the skin and the subcutaneous capillaries, and (2) the varying force that may throttle the blood flow in the capillaries. In the prior art, designing a product with the proper force (high enough to prevent an air gap between sensor and skin, low enough to prevent throttling the capillaries) has posed a difficult challenge, especially since human ears differ greatly over the population.

In the prior art, several methods have been tried to suppress the effect of motion artifacts with limited success. For example, the inventor has recognized filtering is difficult since when a person runs, the motion artifact corresponds to the cadence frequency which is well within the range of the heart rate signal. That is why also other mathematical algorithms fail when heavy motion artifact is present. The use of acceleration sensors has been described to compensate for the motion artifact. However, acceleration sensors detect absolute force, which is not necessarily related to the relative distance variation Δd between the sensor and the blood vessel.

In one prior art system, the use of two sensors, one in each ear, is described. By applying diversity, the idea is that the heart rate signals from two sensors, located at each ear, constructively add, whereas noise and other interference (like motion artifact) cancels. For a cancellation, it is necessary that the desired signal (i.e. the heart rate signal) is correlated and all other signals are uncorrelated. Examples of uncorrelated signals that may be compensated for are (1) random noise, (2) ambient light (e.g., sunlight). Unfortunately, the motion artifact experienced at the left and right ear is highly correlated. As such, the inventor has recognized the use of one sensor at each ear does not, by itself, provide an optimal solution.

In contrast, in the inventive methods and systems described herein, the motion artifact experienced at the left ear is designed to be uncorrelated to the motion artifact experienced at the right ear as much as possible. This is accomplished by using an asymmetric setup where the sensor in the left ear is located and oriented in a different fashion than the sensor in the right ear. Although the movement of the head on the right side and on the left side is highly correlated, the impact on the sensors is not. Advantageously, improved heart rate detection performance is obtained by reducing the impact of motion artifacts and noise.

In one example of the invention, a headphones apparatus includes a left earbud dimensioned for positioning proximate a left ear canal of a wearer. The left earbud includes a left earbud body, a left electroacoustic transducer arranged to deliver sound to the left ear canal, a left light emitter oriented at the left earbud body to emit a first light directed in a first direction at a left ear location, and a left light detector oriented at the left earbud body to detect a detected first light following interaction of the first light with a left ear tissue.

The headphones apparatus further include a right earbud dimensioned for positioning proximate a right ear canal of a wearer. The right earbud includes a right earbud body, a right electroacoustic transducer arranged to deliver sound to the right ear canal, a right light emitter oriented at the right earbud body to emit a second light in a second direction directed at a right ear location, where the right ear location is different from the left ear location or the second direction is different from the first direction. The right earbud includes a right light detector oriented at the right earbud body to detect a detected second light following interaction of the second light with a right ear tissue.

In one example, a method includes emitting a first light in a first light direction directed at a left ear location from a left ear light emitter, and detecting a detected first light at a left ear light detector following interaction of the first light with a left ear tissue. The method includes emitting a second light in a second light direction directed at a right ear location from a right ear light emitter, where the right ear location is different from the left ear location or the second light direction is different from the first light direction. The method further includes detecting a detected second light at a right ear light detector following interaction of the second light with a right ear tissue, and estimating a heart rate from the detected first light and the detected second light.

In one example, a headphones apparatus includes a left earbud dimensioned for positioning proximate a left ear canal of a wearer. The left earbud includes a left earbud body, a left electroacoustic transducer arranged to deliver sound to the left ear canal, and a left heart rate sensor arranged at a first position at the left earbud body. The headphones apparatus includes a right earbud dimensioned for positioning proximate a right ear canal of the wearer. The right earbud includes a right earbud body, a right electroacoustic transducer arranged to deliver sound to the right ear canal, and a right heart rate sensor arranged at a second position at the right earbud body, wherein the first position at the left earbud body is different than the second position at the right earbud body.

Figure 7:
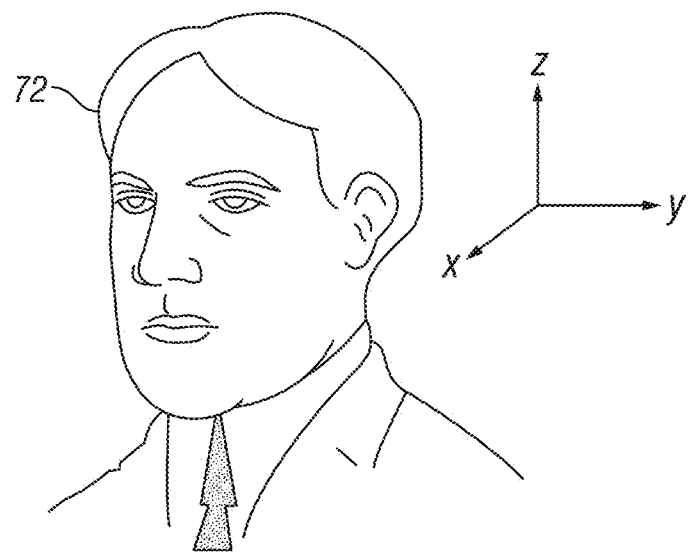
FIG. 7 illustrates an XYZ axis with respect to an earphones wearer's head.
Figure 18:
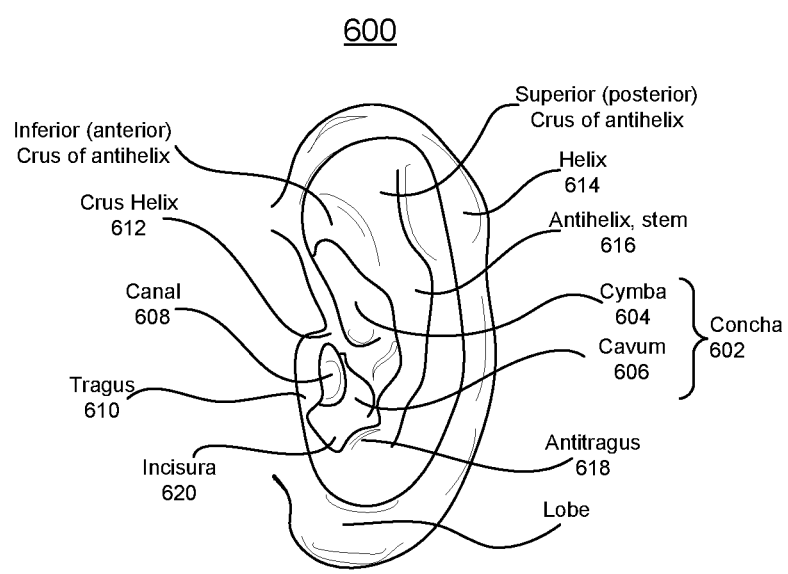
FIG. 18 illustrates the anatomy of a human ear.

In various examples described herein, the orientation on the XYZ-axis as shown in FIG. 7, where the X-axis is in the horizontal direction in parallel to a user head 72 (i.e., from back of the head to the face), the Y-axis is in the horizontal direction perpendicular to the head 72 (i.e., from right ear to left ear), and the Z-axis is in the vertical direction (i.e., from toe to head). One of ordinary skill will recognize the XYX-axis can be defined in any desired manner with respect to the wearer. FIG. 18 illustrates the anatomy of a human ear.

Figure 8:
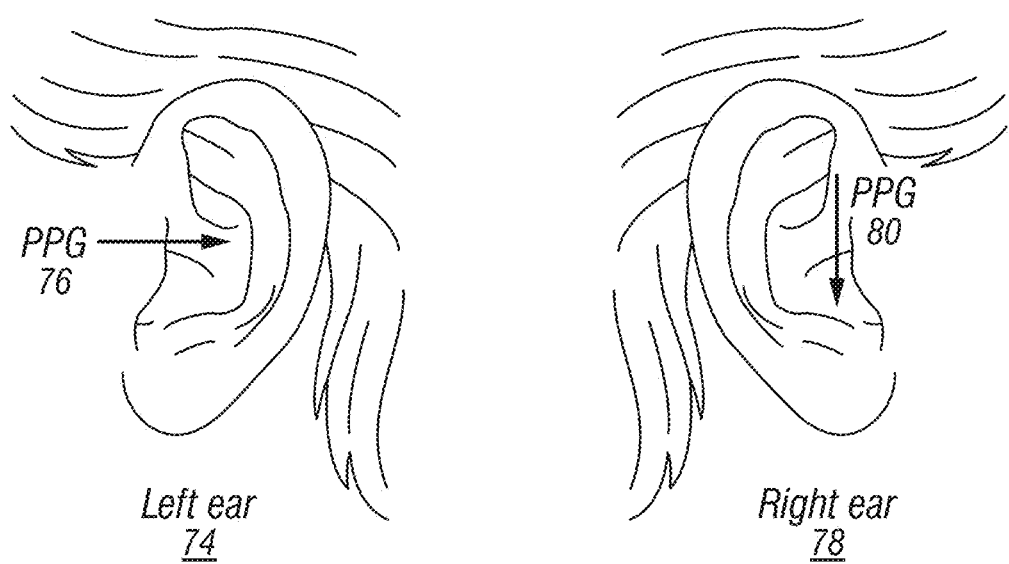
FIG. 8 illustrates an output direction of a left ear PPG sensor in a first direction and an output direction of a right ear PPG sensor in a second direction different from the first direction.

In one example, the configurations for the PPG sensors in the left and right ears are made as asymmetric as possible. For example, the PPG sensor in the right ear may be operating along the Y-axis (horizontal, perpendicular to the head), pointing the light to the concha. In contrast, the PPG sensor in the left ear may be operating along the X-axis (horizontal, in parallel to the head) pointing the light in the tragus or anti-tragus (Z-axis). FIG. 8 illustrates an output direction of a left ear 74 PPG sensor in a first direction 76 and an output direction of a right ear 78 PPG sensor in a second direction 80 different from the first direction 76. In FIG. 8, an embodiment with a horizontal orientation (concha) in the left ear 74 and vertical direction (anti-tragus) in the right ear 78 is visualized.

Although the motion artifact effects in the left ear and right ear are experienced in orthogonal directions, there may still be a correlated motion artifact component left, experienced in the same way at both ears. Further improvement may be obtained by the use of acceleration sensors integrated in both earbuds. Since the mutual orientation of the PGG sensor and acceleration sensor is fixed and known (since they are both part of the same earbud), the signals from the acceleration sensor will reveal in which direction the movement is biggest. This information can be used to de-correlate the left and right PPG signals in order to facilitate the reduction of the motion artifact effects. In addition, it can be used to apply a proper weight on the individual PPG signals when combining. For example, when the acceleration sensor detects movement which is mostly perpendicular to the measurement direction of the corresponding PPG sensor, this PPG signal is prioritized more than when the acceleration sensor detects movement in the measurement direction of the PPG sensor.

Figure 12:
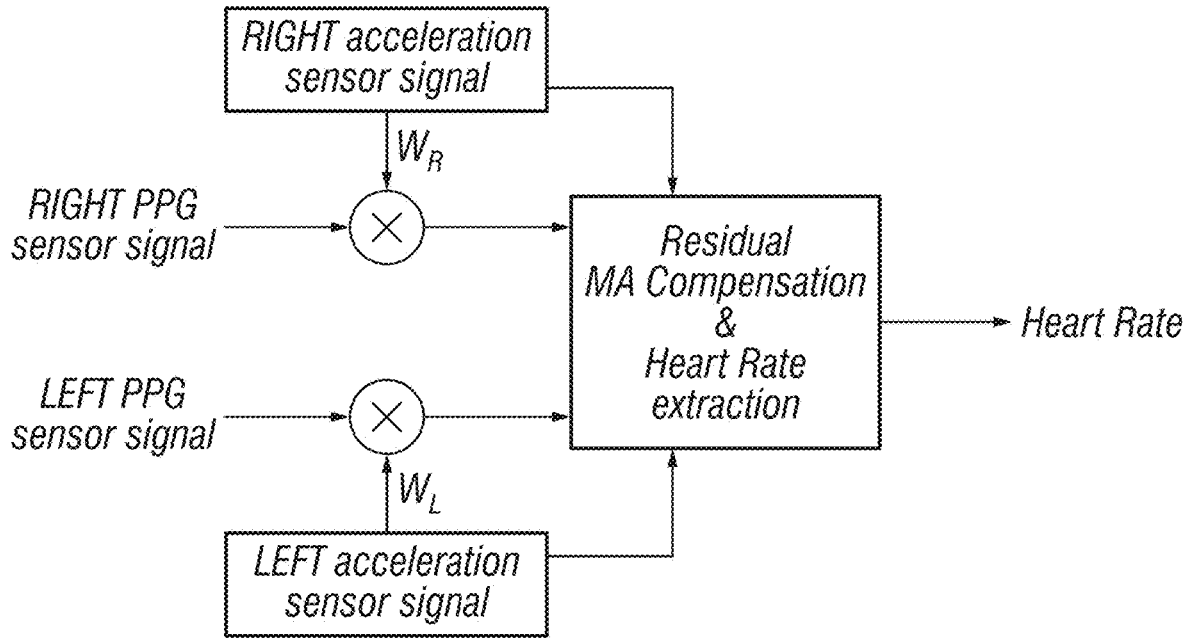
FIG. 12 illustrates processing of a left ear PPG sensor signal output and a right ear PPG sensor signal output together with acceleration sensor signals to estimate a user heart rate.

FIG. 12 illustrates processing of a left ear PPG sensor signal output and a right ear PPG sensor signal output together with acceleration sensor signals to estimate a user heart rate. In FIG. 12, a high-level schematic diagram is shown, where $W_L$ and $W_R$ represent the weight factor prioritizing the left or right PPG sensor signals based on the left and right acceleration sensor signals, respectively. In the processing unit indicated by "Residual MA Compensation & Heart Rate extraction" the weighted PPG signals are combined. Uncorrelated interference is removed, and information from the acceleration sensors can give further information about the reliability and quality of the individual PGG signals. That is, higher quality signals are prioritized over lower quality signals.

Figure 13:
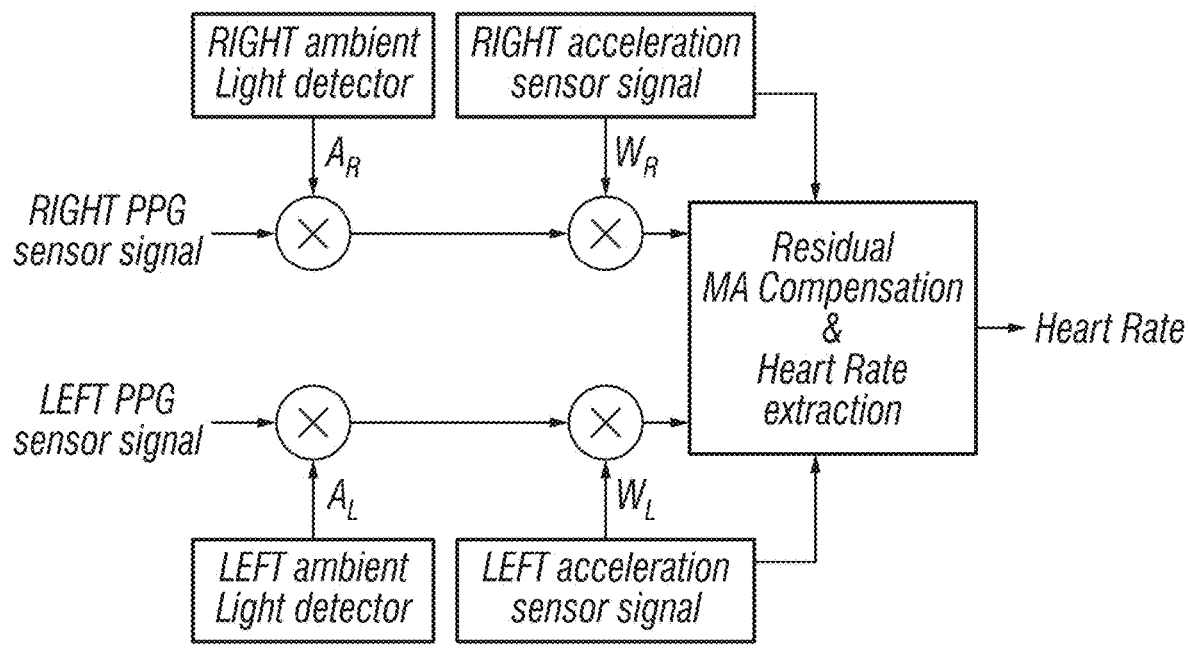
FIG. 13 illustrates processing of a left ear PPG sensor signal output and a right ear PPG sensor signal output together with acceleration sensor signals and ambient light sensor signals to estimate a user heart rate.

Other interference sources which are uncorrelated by nature will also be cancelled by the system shown in FIG. 12. As an example, ambient light is an interference which is mostly uncorrelated between left and right (if sunlight is directly hitting the left side of the head, the right side of the head is in the shadow of the head). When strong external light (for example sunlight) reaches the photo detector of the PPG sensor, the measurement can be disturbed severely. This is due to the fact that ambient light creates a strong DC component which may saturate the photo detector. That will reduce the dynamic range of the detector, reducing the sensitivity for heart rate signals. Measuring ambient light, either explicitly with an additional photo detector close to the PPG photo detector or implicitly by measuring the DC current in the PPG photo detector, can be used to again to weigh the PPG sensor signals. That is, the PPG sensor experiencing the lowest ambient light will be prioritized above the PPG sensor experiencing more ambient light. This is also visualized in FIG. 13 with weight factors $A_R$ and $A_L$. FIG. 13 illustrates processing of a left ear PPG sensor signal output and a right ear PPG sensor signal output together with acceleration sensor signals and ambient light sensor signals to estimate a user heart rate.

Figure 14A:
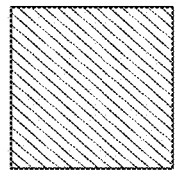
FIGS. 14a and 14b illustrate the use of more than two PPG sensor signal outputs to estimate a user heart rate.
Figure 14A:
Figure 14B:
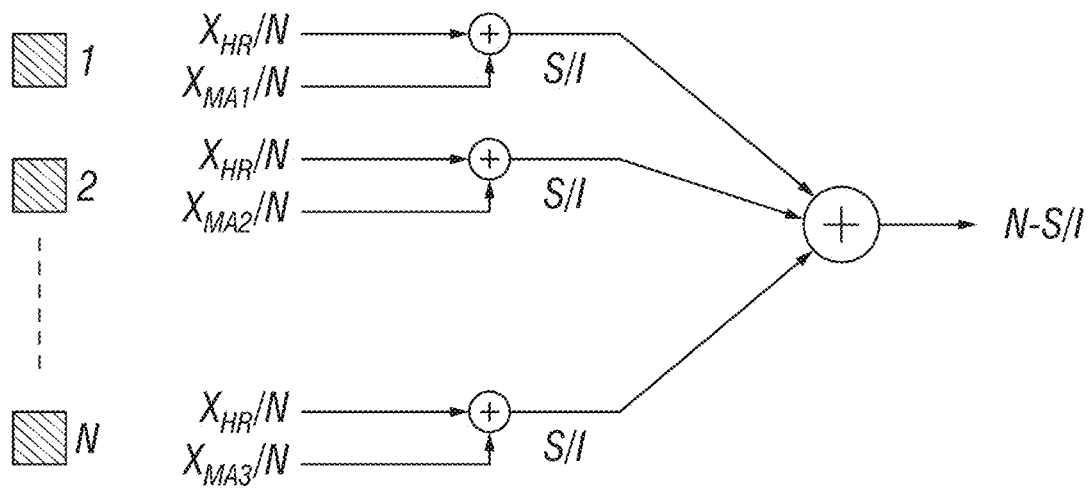

It will be understood that the concept can be extended to more than two PPG sensors, the sensors being placed at different (asymmetric between left and right ear) positions in the ears. The LED and photo detection can be further miniaturized to allow more of them in a headphones apparatus. Although the detection sensitivity of a smaller photo detector deteriorates, the combined effect of all the photo detectors together (and taking into account many uncorrelated interference signals, i.e. the interference is distributed over many different locations and therefore uncorrelated) will provide a better overall performance. This concept is visualized in FIGS. 14a and 14b. In FIG. 14a, a single sensor system is shown with the HR signal $x_{HR}$ disturbed by the interference $x_{MA}$. By splitting up this system into N smaller sub-systems, the strengths of intended and interfering signals decrease due to the reduced area of the sensor. However, if the total detection area of the distributed system shown in FIG. 14b is identical to the detection area of the single system shown in FIG. 14a, the power of the combined desired signals, signal $x_{HR}$, will not change. However, since the motion artifact component $x_{MA}$ is broken up in N uncorrelated components $x_{MAi}/N$, the final Signal-to-Interference ratio (S/I) for the distributed system will be N times as high as the S/I of the single system.

In the methods and apparatuses of the invention, the use of a dual-sensor provides two-path diversity. The common signal on both paths is the heartrate (HR) signal. The heart rate signals detected by both sensors should be highly correlated. In contrast, any disturbance and interference picked up by one sensor should be uncorrelated to any disturbance and interference picked up by the other sensor. This is accomplished by choosing different sensor positions in the left and right ears such that the interference (mainly caused by motion) experienced in the left ear is uncorrelated from the interference experienced in the right ear. In one example, the system is based on PPG, an optical detection technique with light emitted by a LED reflecting on the human skin where it is modulated by the pulsation of the blood stream and is detected by a photo detector. In PPG, most interference is cause by motion in the direction of the light signal. Other sensing system may be used in further examples. Based on the sensing principle, the location and orientation of the sensors should be chosen such that desired signals add constructively, and interfering signals cancel each other as much as possible. In one example, sensors using different sensing principles can be used. For example, one sensor may use reflective PPG and the other sensor may use transmissive absorption PPG. In another embodiment, one sensor may use an optical method (like PPG), whereas the other sensor may use a different physical measurement principle, e.g. measuring electrical potentials. The signals representing the HR will be highly correlated and can be combined constructively. The motion artifact effects will most likely be completely different in case of different sensing methods, thus successful suppression of interference is possible.

Figure 16:
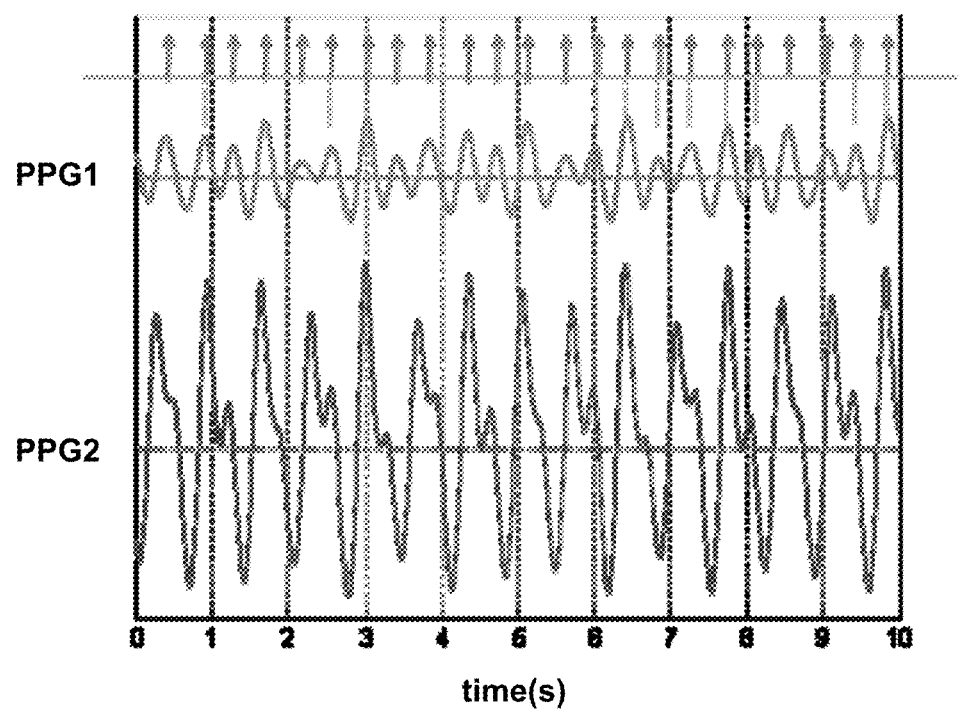
FIG. 16 illustrates sample output signals of a left ear PPG sensor and a right ear PPG sensor.

With a dual-sensor system, two PPG signals, PPG1 and PPG2, are provided by the sensors. FIG. 16 illustrates sample output signals of a left ear PPG sensor and a right ear PPG sensor. FIG. 16 shows an example of PPG1 and PPG2, with PPG2 experiencing quite some motion artifacts. In this example, the basic heartrate is 140 BPM and the user has a step cadence of about 88 (left or right) steps/minute. Since motion artifacts cause an interference which is multiplicative rather than additive, the PPG2 signal looks stronger; yet it has a more irregular pattern from which it is harder to extract the HR.

Figure 9:
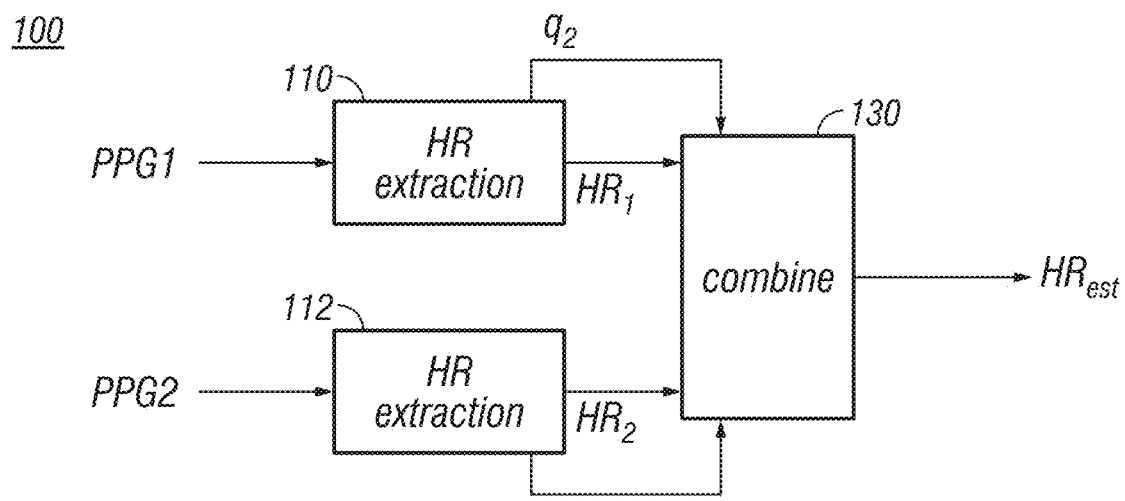
FIG. 9 illustrates processing of a left ear PPG sensor signal output and a right ear PPG sensor signal output to estimate a user heart rate in one example.

Using the two PPG signal streams, the best estimate of the actual HR is made. Different methods exist to achieve this estimation. FIG. 9 illustrates processing of a left ear PPG sensor signal output and a right ear PPG sensor signal output to estimate a user heart rate in one example. In process 100 shown in FIG. 9, each PPG signal is separately processed to obtain a preliminary HR. In the HR extraction blocks 110 and 112, the PPG input is taken and a HR is extracted. The two preliminary HRs, HR1 and HR2, can then be combined in block 130 to arrive at the estimated $HR_{est}$. For example, simply the average of the preliminary HRs can be taken, which is also known as equal-gain combining:

$$HR_{est} = \frac{HR_1 + HR_2}{2}$$

In a more sophisticated combining, a weighted average is taken where the weights are determined by a quality measure. For example, the Signal-to-Noise Ratio (SNR) or Signal-to-Interference Ratio (SIR) experienced in blocks 110 and 112 can be used as quality measures to weight the signals in such a way that the signal with the highest SNR (SIR) is weighted with a higher weight (this is also known as maximum ratio combining):

$$HR_{est} = \frac{q_1 HR_1 + q_2 HR_2}{q_1 + q_2}$$

The values q1 and q2 are the weighting factors and range between 0 and 1. These quality measures can also come from other sources. For example, an acceleration sensor output may indicate how much motion is experienced in the direction of measurement in the sensor. Alternatively, or in addition, an ambient light detector may indicate how much environmental light is hitting the sensor.

Figure 10:
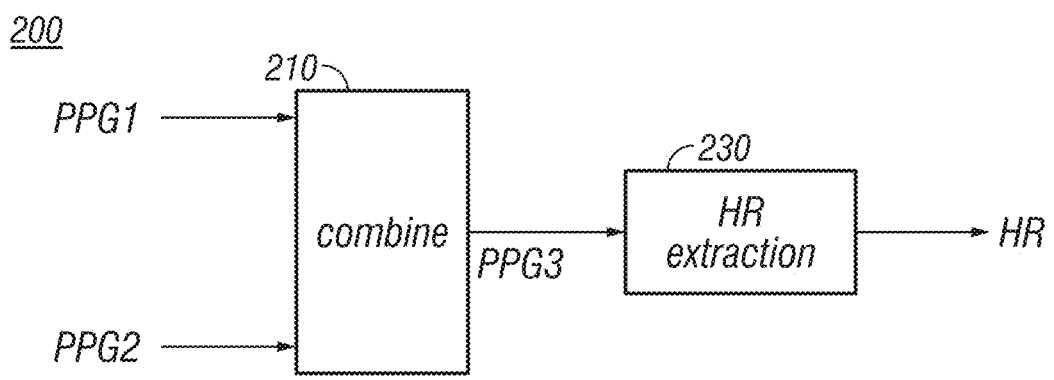
FIG. 10 illustrates processing of a left ear PPG sensor signal output and a right ear PPG sensor signal output to estimate a user heart rate in a further example.

FIG. 10 illustrates processing of a left ear PPG sensor signal output and a right ear PPG sensor signal output to estimate a user heart rate in a further example. In process 200 shown in FIG. 10, the two PPG signals are combined in block 210 before HR extraction takes place in block 230. The combination can be achieved in a similar fashion as discussed above, i.e. using equal-gain or maximum ratio combining, or some other combining technique. The idea is that after combining, the PPG3 signal is cleaner and contains less interference. This will increase the reliability of the HR extraction in block 230. The processing carried out in block 230 is similar to the processing in blocks 110 and 112 in process 100.

Figure 11:
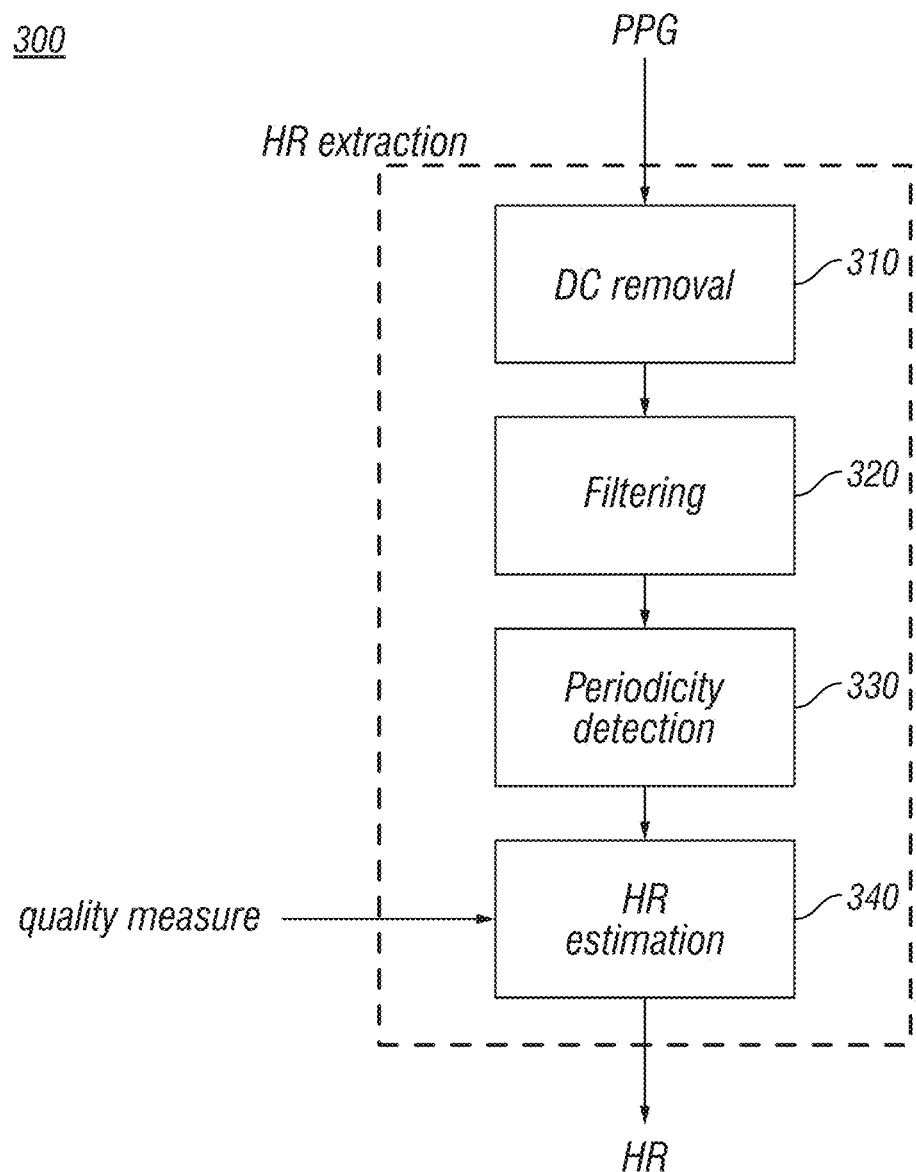
FIG. 11 illustrates a process for extracting a user heart rate in one example.

FIG. 11 illustrates a process 300 for extracting a user heart rate in one example. In process 300, a more detailed description of the HR extraction algorithm carried out in blocks 110, 112 and 230 referenced above in FIG. 9 and FIG. 10 is given in one example. First, the PPG signal is conditioned in order to make it more suitable for HR extraction. At block 310, the DC from the PPG is removed. The DC is caused by constant light falling on the photo detector. This will be the light from the source LED that is modulated by the HR, but additionally it can be ambient light like sunlight when the user is outside. Furthermore, the photo detector output may have a voltage or current offset. Next, at block 320, filtering takes place to filter out all frequency components not related to the heartrate. The HR for humans ranges between 0.5 Hz (30 BPM) and 4 Hz (240 BPM). Any frequency components not in this range can be suppressed.

The filtered signal PGG signal that remains is a periodic signal with the fundamental frequency corresponding to the HR, shown in FIG. 16. At block 330, the period T in the signal needs to be determined. The HR in BPM is simply 60/T. Different techniques exist to determine the period. One could for example count the number of zero-crossings in a certain interval. One could distinguish between zero-crossings on rising edges and zero-crossings on falling edges. Furthermore, one could count the local maxima (peaks) in a certain time interval or the local minima (bottoms or notches). For example, the upper row with HR triggers shown in FIG. 16 is based on the local maxima found in PPG1 (note that for a HR of 140 BPM, there are about 2.3 beats in one second). More advanced algorithms take into account the alternate sequence of rising a zero-crossing, a peak, a falling zero-crossing, and a bottom. Correlation techniques can be applied to match different references of different periodicity. These methods may use Fourier Transform (FFT) techniques or Continuous Wavelet Transform (CWT) techniques. The higher the signal-to-interference ratio in the PPG signal, the more accurately the periodicity can be estimated.

From the periodicity detection, the HR estimation is derived at block 340. Since a new PPG sample may arrive every 20 ms (50 Hz sampling), an HR estimate can be made every 20 ms using past samples. However, some additional filtering can be added since the HR cannot change instantaneously (there is a time constant in the order of several seconds to tens of seconds to change the human HR by say 10 BPM). The HR estimate can be based on the new estimate and N previous values. The update can be weighted based on a quality measure. If quality is sufficient, the newly found estimate can be given higher weight. In contrast, with noisy signals, more filtering takes place and more past samples are taken into account. As an example, an exponential-forget filter can be used where the new HR estimate $HR_{est}(k+1)$ is based on the most recent found HR value $HR_{new}(k)$ weighted with α and the previous HR estimate $HR_{est}(k)$ weighted with 1−α:

$$HR_{est}(k+1)=\alpha HR_{new}(k)+(1-\alpha)HR_{est}(k)$$

When the quality is low, α may approach towards 0 whereas when the quality is high, α may approach 1.

Figure 1A:
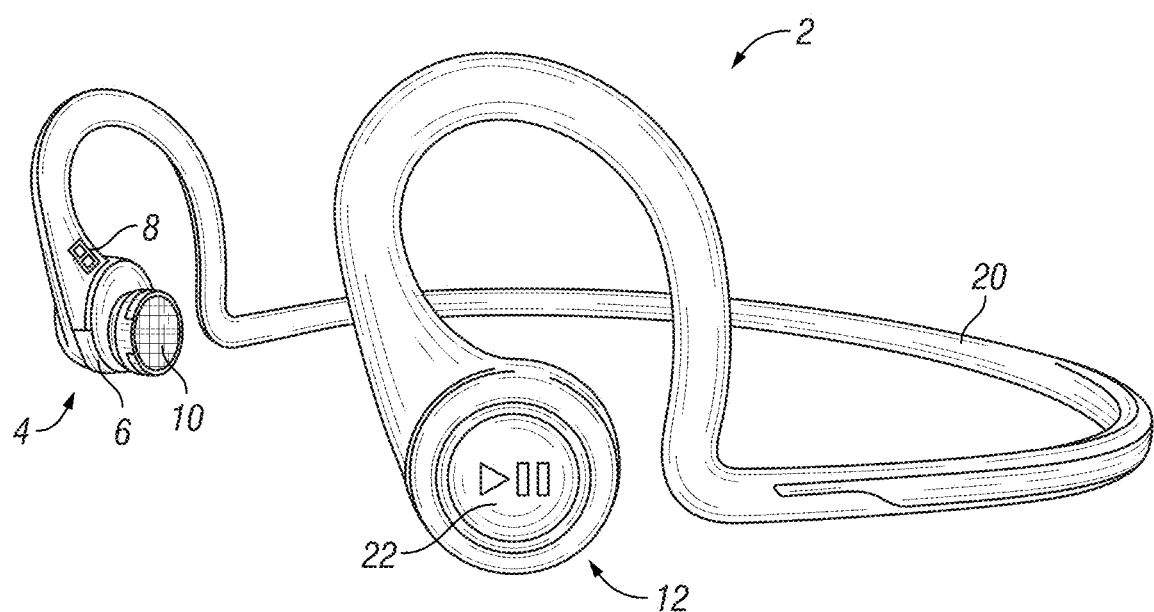
FIGS. 1A and 1B illustrate a left view and right view, respectively, of a headphones apparatus in one example embodiment.
Figure 1B:
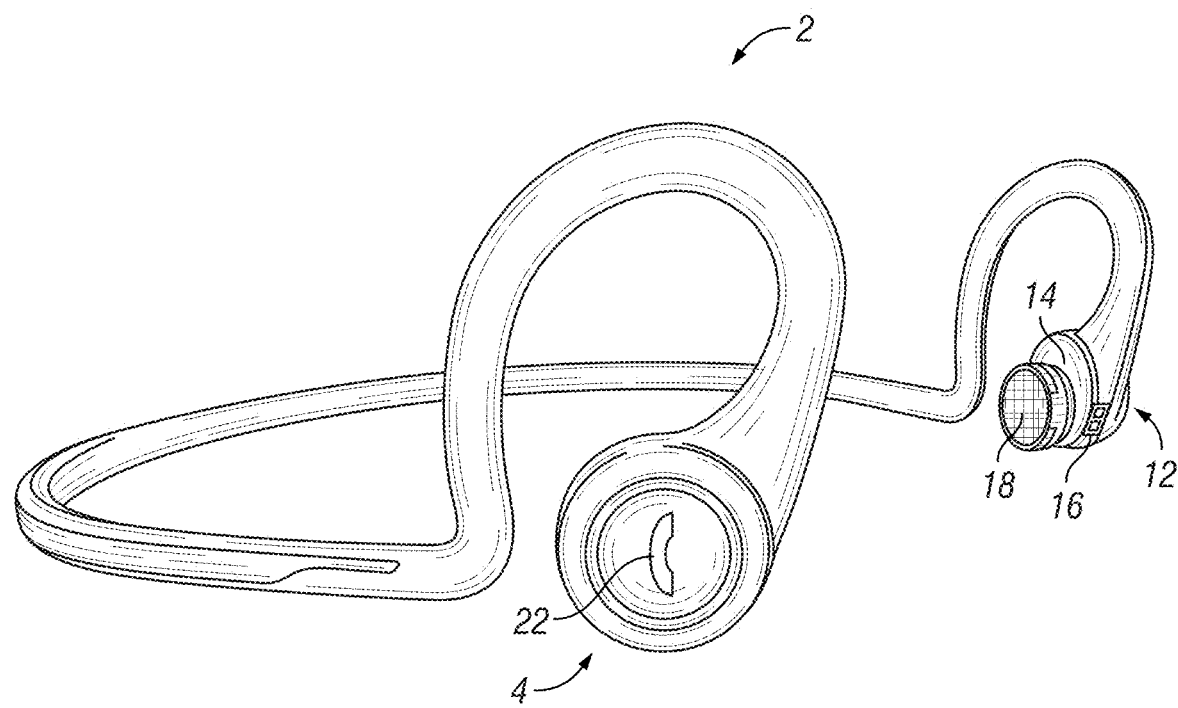

FIGS. 1A and 1B illustrate a left view and right view, respectively, of a headphones apparatus 2 in one example embodiment. Headphones apparatus includes a left earbud 12 dimensioned for positioning proximate a left ear canal of a wearer. The left earbud 12 includes a left earbud body 14, a left electroacoustic transducer 18 (e.g., a speaker) arranged to deliver sound to the left ear canal, and a left photoplethysmographic (PPG) sensor 16 including a left light emitter oriented at the left earbud body 14 to emit a first light directed in a first direction at a left ear location. The left PPG sensor 16 includes a left light detector oriented at the left earbud body 14 to detect a detected first light following interaction of the first light with a left ear tissue.

The headphones apparatus 2 further include a right earbud 4 dimensioned for positioning proximate a right ear canal of a wearer. The right earbud 4 includes a right earbud body 6, a right electroacoustic transducer 10 (e.g., a speaker) arranged to deliver sound to the right ear canal, and a right photoplethysmographic (PPG) sensor 8 including a right light emitter oriented at the right earbud body 6 to emit a second light in a second direction directed at a right ear location. The right PPG sensor 8 includes a right light detector oriented at the right earbud body 6 to detect a detected second light following interaction of the second light with a right ear tissue.

In one example, the right ear location is different from the left ear location. For example, the left ear location is a tragus area or an anti-tragus area and the right ear location comprises a concha area. In a further example, the left ear location is a concha area and the right ear location comprises a tragus area or an anti-tragus area. In this example, the left PPG sensor 16 is located at a different corresponding location on the left earbud body 14 as the right PPG sensor 8 is on the right earbud body 6. For example, the left PPG sensor 16 is located on a lower front surface on left earbud body 14 and the right PPG sensor 8 is located on an upper side surface on right earbud body 6

In one example, the second direction of the second light emitted by the right light emitter is different from the first direction of the first light emitted by the left emitter. The corresponding right ear location may be the same as the left ear location. For example, the first light and second light may both be directed at a tragus area, but at different directions (i.e., angles). The left PPG sensor 16 may be located at a same corresponding location on the left earbud body 14 as the right PPG sensor 8 is on the right earbud body 6, but the left light emitter is oriented (i.e., pointed or angled) to output light in a different direction with respect to the left ear than the right light emitter is oriented to output light with respect to the right ear.

In one example, the first direction of the first light is different from the second direction of the second light. In one example, the first direction is substantially perpendicular to the second direction. For example: (a) the first direction is along an x-axis and the second direction is along a y-axis or a z-axis, (b) the first direction is along a y-axis and the second direction is along an x-axis or a z-axis, or (c) the first direction is along a z-axis and the second direction is along an x-axis or a y-axis.

Earbud 4 and earbud 12 are coupled by a connector 20. In one example, connector 20 is a flexible electrical cable. The rigidity of the flexible electrical cable may be varied. Headphones apparatus 2 also includes a microphone for receiving user speech. Although the examples herein refer to the use of an earbud form factor, other form factors known in the art for outputting an audio signal to a user ear may be used, such as an over-the-ear form factor.

In one example, the left earbud 12 further includes a left motion sensor and the right earbud 4 further includes a right motion sensor. For example, the motion sensors may be three axis accelerometers. In one example, the left earbud 12 further includes a left ambient light sensor and the right earbud 4 further includes a right ambient light sensor.

Although illustrated as wireless headphones, headphones apparatus 2 may also be corded headphones. Furthermore, although headphones apparatus 2 may be referred to and described as a telecommunications headset in certain examples, the examples described herein throughout are applicable to headphones (also referred to as earphones, stereophones, headsets, and earbuds) having listen only functionality.

Figure 2A:
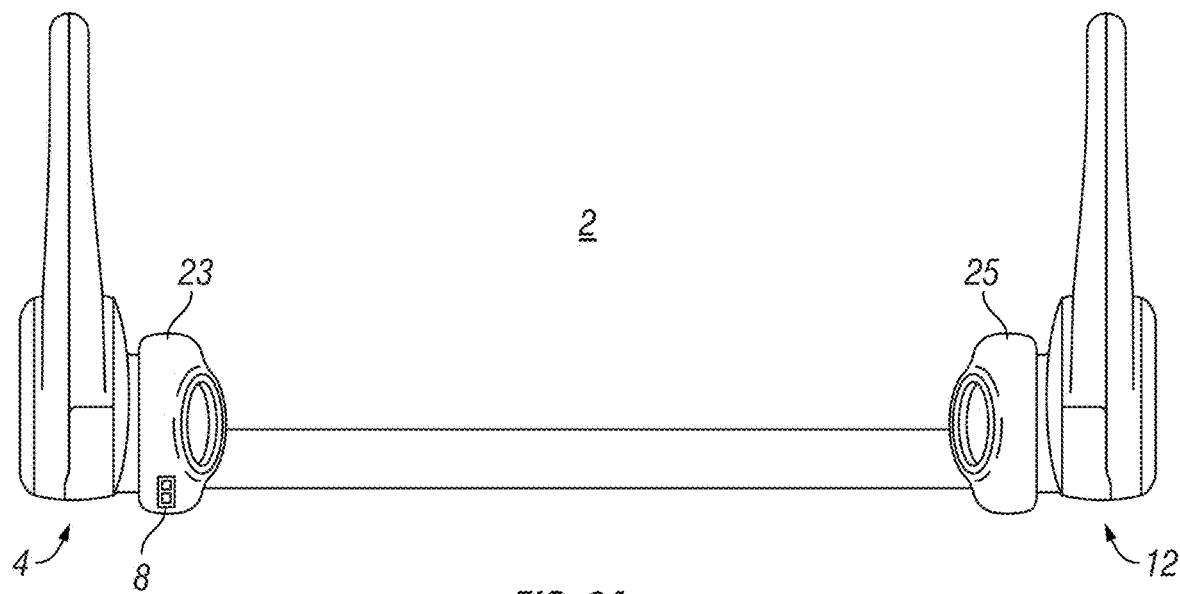
FIGS. 2A and 2B illustrate a front view and rear view, respectively, of a headphones apparatus in one example embodiment showing an alternative placement of the PPG sensors.
Figure 2B:
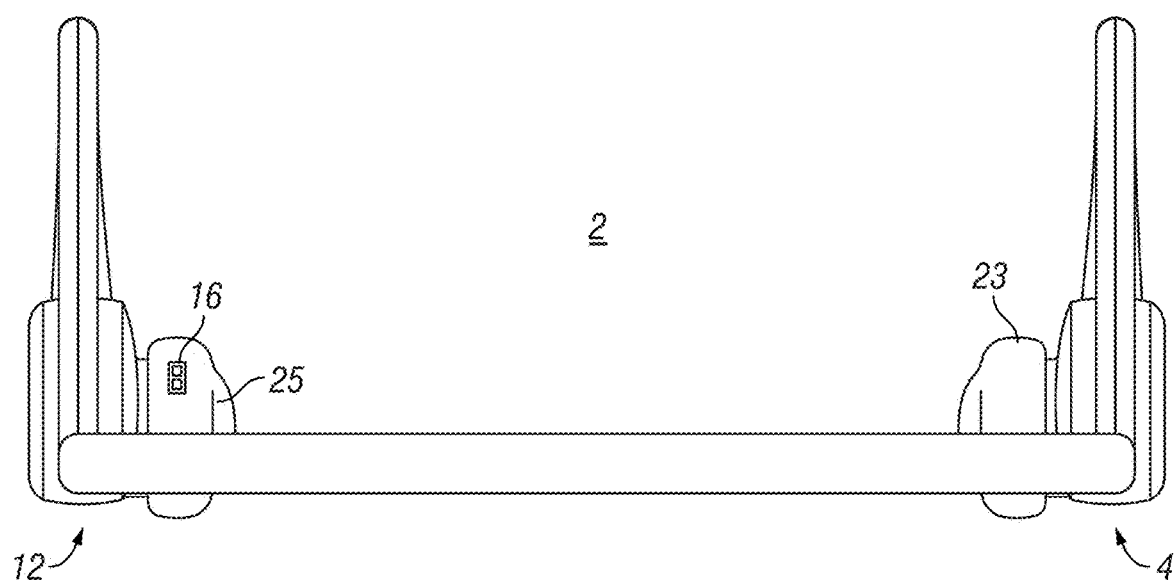

FIGS. 2A and 2B illustrate a front view and rear view, respectively, of the headphones apparatus 2 in one example embodiment showing an alternative placement of the PPG sensors. In this example, the light emitter of right PPG sensor 8 is oriented at the right earbud body to emit light directed forward and down into the trachus of the right ear. The light emitter of left PPG sensor 16 is oriented at the left earbud body 14 to emit light directed backwards and up into the conchae of the left ear.

The left earbud 12 further includes a left ear tip 25 dimensioned to attach to the left body, the left ear tip 25 having one or more apertures through which the left emitter light passes. The left ear tip 25 also includes an ear canal port to insert into an entrance of the left ear canal. Similarly, the right earbud 4 further includes a right ear tip 23 dimensioned to attach to the right body, the right ear tip 23 having one or more apertures through which the right emitter light passes. The right ear tip also includes an ear canal port to insert into an entrance of the right ear canal.

Figure 3:
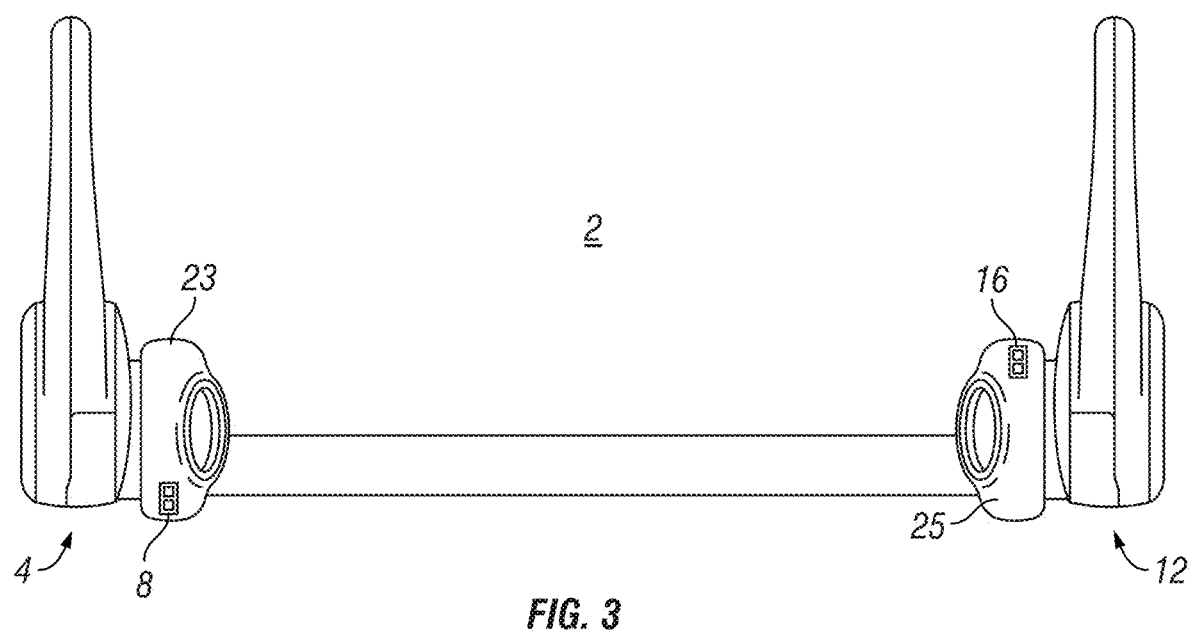
FIG. 3 illustrates a headphones apparatus in one example embodiment showing an alternative placement of the PPG sensors.

FIG. 3 illustrates the headphones apparatus 2 in one example embodiment showing an alternative placement of the PPG sensors. In this example, the light emitter of right PPG sensor 8 is oriented at the right earbud body 4 to emit light directed into the trachus of the right ear. The light emitter of left PPG sensor 16 is oriented at the left earbud body 14 to emit light directed at the conchae of the left ear.

Figure 4:
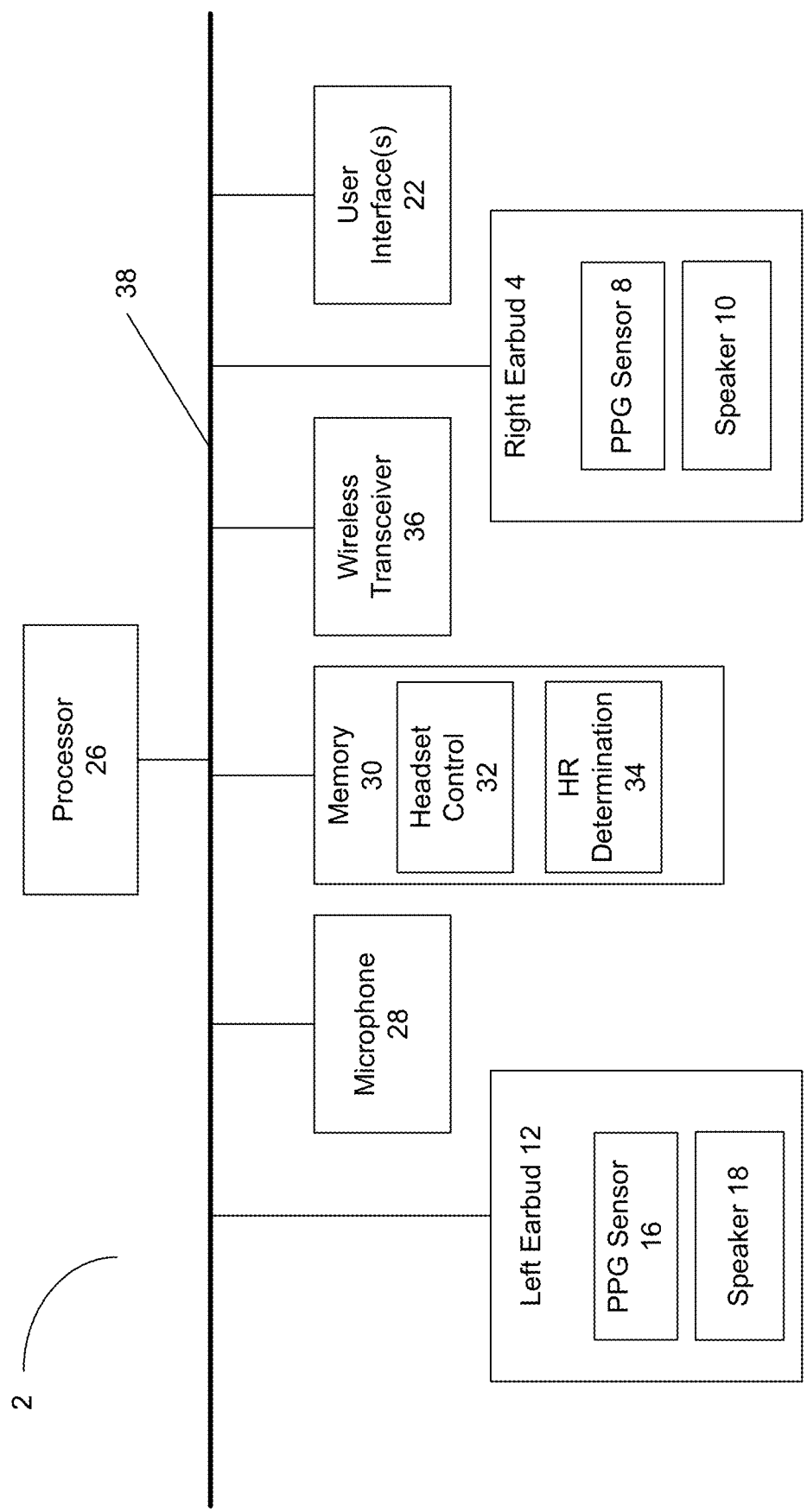
FIG. 4 shows a simplified block diagram of the headphones apparatus shown in FIG. 1A and FIG. 1B in one example.

FIG. 4 shows a simplified block diagram of the headphones apparatus 2 shown in FIG. 1A and FIG. 1B in one example. Headphones apparatus 2 includes a processor 26 operably coupled via an interconnect 38 to a heart rate determination module 34, memory 30, microphone 28, wireless transceiver 36, user interface(s) 22, left earbud 12, and right earbud 4. Left earbud 12 includes a PPG sensor 16 and speaker 18. Right earbud 4 includes a PPG sensor 8 and speaker 10. Wireless transceiver 36 may, for example, be a Bluetooth transceiver. A headset control application 32 resides in memory 30. Headset control application 32 is executed by processor 26. In one example, memory 30 may store heart rate determination module 34, and output data from PPG sensor 16 and PPG sensor 8.

Memory 30 may include a variety of memories, and in one example includes SDRAM, ROM, flash memory, or a combination thereof. Memory 30 may further include separate memory structures or a single integrated memory structure. In one example, memory 30 may be used to store passwords, network and telecommunications programs, and/or an operating system (OS).

Processor 26 allows for processing data, in particular managing data between left earbud 12, right earbud 4, headset control application 32, heart rate determination module 34, user interface(s) 22, wireless transceiver 36, microphone 28, and memory 30. Heart rate determination module 34 (e.g., an application program executed by processor 26) receives an output signal from the PPG sensor 16 at left earbud 12 and an output signal from PPG sensor 8 at right earbud 4, and determines the wearer heart rate. Examples of operation of PPG sensor 16, PPG sensor 8, and heart rate determination module 34 include those as described herein in reference to FIG. 6 and FIGS. 9-16.

In one example, processor 26 is a high performance, highly integrated, and highly flexible system-on-chip (SoC), including signal processing functionality such as echo cancellation/reduction and gain control in another example. Processor 26 may include a variety of processors (e.g., digital signal processors), with conventional CPUs being applicable. User interface(s) 22 allow for communication between the headset user and the headset, and in one example includes an audio and/or visual interface such that a prompt may be provided to the user's ear and/or an LED may be lit. User interface(s) 22 may include buttons or touch sensors to receive call answer, power on/off, menu navigation, or multimedia output control user input actions.

Referring to FIG. 1A-1B and FIG. 4 together, in operation heart rate determination module 34 causes PPG sensor 16 to emit a first light in a first light direction directed at a left ear location from a left ear light emitter, and detect a detected first light at a left ear light detector following interaction of the first light with a left ear tissue. Heart rate determination module 34 causes PPG sensor 8 to emit a second light in a second light direction directed at a right ear location from a right ear light emitter, the right ear location different from the left ear location or the second light direction different from the first light direction. PPG sensor 8 detects a detected second light at a right ear light detector following interaction of the second light with a right ear tissue. Heart rate determination module 34 estimates a wearer heart rate from the detected first light and the detected second light. In one example, estimating the heart rate from the detected first light and the detected second light includes determining a quality of the detected first light relative to the detected second light.

Figure 5:
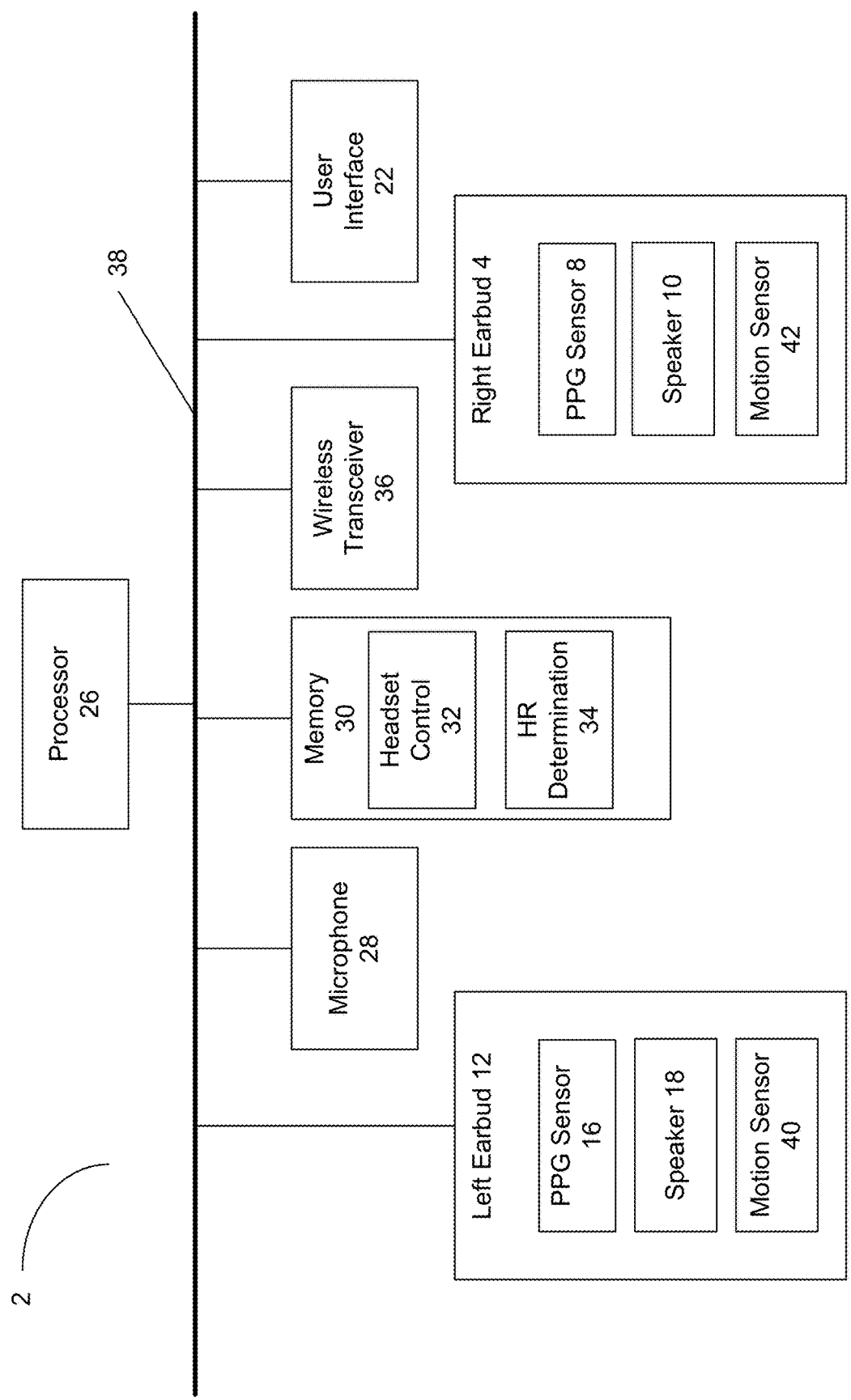
FIG. 5 illustrates a further example of a headphones apparatus.

Referring now to FIG. 5, a further example of a headphones apparatus 2 is illustrated. Headphones apparatus 2 shown in FIG. 5 is substantially similar to that shown in FIG. 4, except that left earbud 12 further includes a motion sensor 40 and right earbud 4 further includes a motion sensor 42, whereby use of motion sensor 40 and motion sensor 42 is described in further detail below. Heart rate determination module 34 is operable to process the output of motion sensor 40 in conjunction with PPG sensor 16 as well as process the output of motion sensor 42 in conjunction with PPG sensor 8 to determine the wearer heart rate.

In one example operation, heart rate determination module 34 receives a left ear motion sensor output and determines a left ear direction of motion from the left ear motion sensor output. Heart rate determination module 34 receives a right ear motion sensor output and determines a right ear direction of motion from the right ear motion sensor output. Heart rate determination module 34 estimates the heart rate from the detected first light and the detected second light by (1) identifying a quality of the detected first light from the left ear direction of motion and the first light direction, and (2) identifying a quality of the detected second light from the right ear direction of motion and the second light direction.

In a further example, heart rate determination module 34 determines a left ear ambient light level proximate or at the left ear light detector, and determines a right ear ambient light level proximate or at the right ear light detector. Heart rate determination module 34 estimates the heart rate from the detected first light and the detected second light by (1) identifying a quality of the detected first light from the left ear ambient light level, and (2) identifying a quality of the detected second light from the right ear ambient light level.

Figure 6:
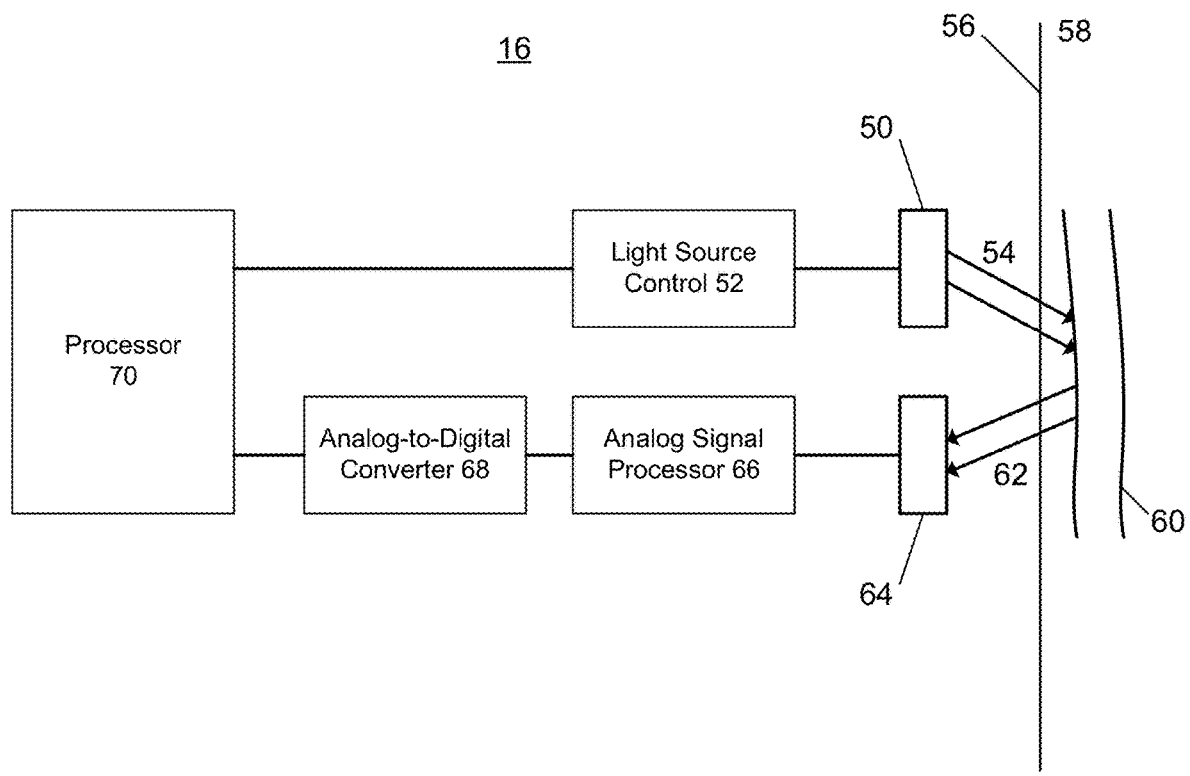
FIG. 6 illustrates a simplified diagram of a PPG sensor in one example arrangement.

FIG. 6 illustrates a simplified diagram of a PPG sensor 16 in one example arrangement. PPG sensor 16 includes a processor 70 (i.e., a microcontroller), light source control 52, one or more light sources 50, light detector 64, analog signal processor 66, and analog-to-digital converter 68. In one example, analog signal processor 66 may include an amplifier. In operation, one or more light sources 50 emit light 54 towards a user skin 56 of the user ear. The intensity of light 54 output by one or more light sources 50 is modified by light source control 52 to maintain a desirable reflected signal intensity. Processor 70 may control light source control 52. Beneath the skin 56, the light 54 contacts blood in the user blood vessel 60, some of which is reflected back as light 62 and detected by light detector 64. The analog output of light detector 64 is processed by analog signal processor 66 and digitized by analog-to-digital converter 68, and the provided to processor 70. PPG sensor 8 is the same or substantially similar.

Figure 15:
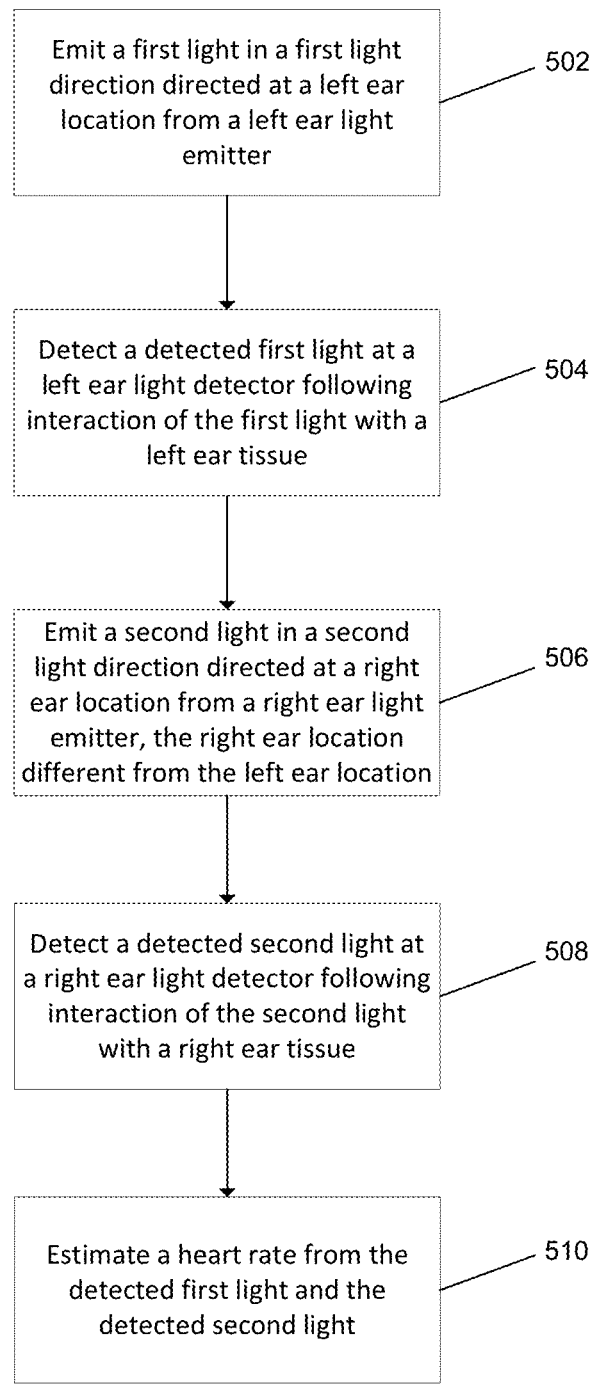
FIG. 15 illustrates a flow diagram for estimating a user heart rate in one example.

FIG. 15 is a flow diagram illustrating a process for estimating a user heart rate in one example. At block 502, a first light is emitted in a first light direction emitted directed at a left ear location from a left ear light emitter. At block 504, a detected first light is detected at a left ear light detector following interaction of the first light with a left ear tissue.

At block 506, a second light is emitted in a second light direction directed at a right ear location from a right ear light emitter, the right ear location different from the left ear location or the second light direction different from the first light direction. At block 508, a detected second light is detected at a right ear light detector following interaction of the second light with a right ear tissue.

In one example, the left ear light emitter and the left ear light detector are components of a left photoplethysmographic sensor and the right ear light emitter and the right ear light detector are components of a right photoplethysmographic sensor. In one example, the left ear location is a tragus area or an anti-tragus area and the right ear location is a concha area. In a further example, the left ear location is a concha area and the right ear location is a tragus area or an anti-tragus area.

In one example, the first light direction is substantially perpendicular to the second light direction. In one example, the first light direction is along an x-axis and the second light direction is along a y-axis or a z-axis. In one example, the first light direction is along a y-axis and the second light direction is along an x-axis or a z-axis. In one example, the first light direction is along a z-axis and the second light direction is along an x-axis or a y-axis.

At block 510, a heart rate is estimated from the detected first light and the detected second light. In one example, the heart rate is estimated from the detected first light and the detected second light by determining a quality of the detected first light relative to the detected second light.

In one example, the process further includes receiving a left ear motion sensor output and determining a left ear direction of motion from the left ear motion sensor output. The process further includes receiving a right ear motion sensor output and determining a right ear direction of motion from the right ear motion sensor output. Estimating the heart rate from the detected first light and the detected second light includes identifying a quality of the detected first light from the left ear direction of motion and the first light direction, and identifying a quality of the detected second light from the right ear direction of motion and the second light direction.

In one example, the process further includes determining a left ear ambient light level proximate or at the left ear light detector. The process further includes determining a right ear ambient light level proximate or at the right ear light detector. Estimating the heart rate from the detected first light and the detected second light includes identifying a quality of the detected first light from the left ear ambient light level, and identifying a quality of the detected second light from the right ear ambient light level.

FIG. 18 illustrates a human ear 600. The outer ear, or pinna, is an irregularly concave cartilaginous member comprised of a number of eminences and depressions which give each ear a distinct shape and form. The helix 614 is the curved outer rim of the ear; below the helix 614 is the anti-helix 616, a curved prominence which describes a curve around the concha 602, a deep cavity containing the entry to the ear canal 608. The concha 602 is divided into two parts, the cymba concha 604 and cavum concha 606, by the crus helix 614 which curves around the outside of the ear, and extends inwards at about the vertical midpoint of the ear. The cymba concha 604 lies above the crus helix 614 and below the anti-helix 616; the cavum concha 606 lies below the crus helix 614 and surrounds the entry to the ear canal 608. In front of the cavum concha 606 and projecting backwards from the front of the ear is the tragus 610, a small semicircular prominence. Opposite the tragus 610 and separated from it by the deep curvature of the incisura 620 is the antitragus 618.

While the exemplary embodiments of the present invention are described and illustrated herein, it will be appreciated that they are merely illustrative and that modifications can be made to these embodiments without departing from the spirit and scope of the invention. Acts described herein may be computer readable and executable instructions that can be implemented by one or more processors and stored on a computer readable memory or articles. The computer readable and executable instructions may include, for example, application programs, program modules, routines and subroutines, a thread of execution, and the like. In some instances, not all acts may be required to be implemented in a methodology described herein. In various embodiments, the techniques of FIGS. 9-15 discussed above may be implemented as sequences of instructions executed by one or more electronic systems. The instructions may be stored by the headphones apparatus 2 or the instructions may be received by the headphones apparatus 2 (e.g., via a network connection).

Terms such as "component", "module", "circuit", and "system" are intended to encompass software, hardware, or a combination of software and hardware. For example, a system or component may be a process, a process executing on a processor, or a processor. Furthermore, a functionality, component or system may be localized on a single device or distributed across several devices. The described subject matter may be implemented as an apparatus, a method, or article of manufacture using standard programming or engineering techniques to produce software, firmware, hardware, or any combination thereof to control one or more computing devices.

Thus, the scope of the invention is intended to be defined only in terms of the following claims as may be amended, with each claim being expressly incorporated into this Description of Specific Embodiments as an embodiment of the invention.

What is claimed is:

1. A headphones apparatus comprising:
 a left earbud dimensioned for positioning proximate a left ear canal of a wearer, comprising:
  a left earbud body;
  a left electroacoustic transducer arranged to deliver sound to the left ear canal;
  a left light emitter oriented positioned at the left earbud body to emit a first light directed in a first direction at a left ear location;
  a left light detector oriented positioned at the left earbud body to detect a detected first light following interaction of the first light with a left ear tissue; and
 a left accelerometer sensor to provide a left accelerometer sensor output indicating a left ear direction of motion;
 a right earbud dimensioned for positioning proximate a right ear canal of the wearer, comprising:
  a right earbud body;
  a right electroacoustic transducer arranged to deliver sound to the right ear canal;
  a right light emitter positioned at the right earbud body to emit a second light directed in a second direction at a right ear location, wherein the right ear location is different from the left ear location or the second direction is different from the first direction; and
  a right light detector positioned at the right earbud body to detect a detected second light following interaction of the second light with a right ear tissue; and
  a right accelerometer sensor to provide a right accelerometer sensor output indicating a right ear direction of motion;
 a processor; and
 a memory comprising computer-executable instructions stored thereon which, when executed by the processor, cause the processor to perform operations comprising:
  determining a first wearer heart rate utilizing the detected first light;
  determining a second wearer heart rate utilizing the detected second light;
  applying a left weight factor to the first wearer heart rate utilizing the left accelerometer sensor output to generate a weighted first heart rate;
  applying a right weight factor to the second wearer heart rate utilizing the right accelerometer sensor output to generate a weighted second heart rate; and
  determining a composite wearer heart rate utilizing the weighted first heart rate and the weighted second heart rate.

2. The headphones apparatus of claim 1, wherein the left earbud further comprises a left ear tip dimensioned to attach to the left earbud body, the left ear tip comprising one or more apertures through which the first light passes, and wherein the right earbud further comprises a right ear tip dimensioned to attach to the right earbud body, the right ear tip comprising one or more apertures through which the second light passes.

3. The headphones apparatus of claim 2, wherein the left ear tip comprises a left ear canal port to insert into an entrance of the left ear canal and the right ear tip comprises a right ear canal port to insert into an entrance of the right ear canal.

4. The headphones apparatus of claim 1, wherein the left ear location comprises a tragus area or an anti-tragus area and the right ear location comprises a concha area.

5. The headphones apparatus of claim 1, wherein the left ear location comprises a concha area and the right ear location comprises a tragus area or an anti-tragus area.

6. The headphones apparatus of claim 1, wherein the left light emitter and the left light detector are components of a left photoplethysmographic sensor and the right light emitter and the right light detector are components of a right photoplethysmographic sensor.

7. The headphones apparatus of claim 1, wherein the left earbud further comprises a left ambient light sensor and the right earbud further comprises a right ambient light sensor.

8. The headphones apparatus of claim 1, wherein the first direction is substantially perpendicular to the second direction.

9. The headphones apparatus of claim 1, wherein the first direction is along an x-axis and the second direction is along a y-axis or a z-axis with respect to a wearer head.

10. The headphones apparatus of claim 1, wherein the first direction is along a y-axis and the second direction is along an x-axis or a z-axis with respect to a wearer head.

11. The headphones apparatus of claim 1, wherein the first direction is along a z-axis and the second direction is along an x-axis or a y-axis with respect to a wearer head.

12. The headphones apparatus of claim 1, wherein the left light emitter and left light detector are located at a same corresponding location on the left earbud body as the right light emitter and right light detector are on the right earbud body.

13. The headphones apparatus of claim 1, wherein the right ear location and the left ear location is at a same anatomical feature, and the first direction is different from the second direction.

14. The headphones apparatus of claim 1, wherein the left light emitter and left light detector are located at a different corresponding location on the left earbud body as the right light emitter and right light detector are on the right earbud body.

15. A headphones apparatus comprising:
 a left earbud dimensioned for positioning proximate a left ear canal of a wearer, comprising:
  a left earbud body;
  a left electroacoustic transducer arranged to deliver sound to the left ear canal; and
  a left heart rate sensor arranged at a first position at the left earbud body to provide a left heart rate sensor output; and
  a left accelerometer sensor to provide a left accelerometer sensor output indicating a left ear direction of motion;
 a right earbud dimensioned for positioning proximate a right ear canal of the wearer, comprising:
  a right earbud body;
  a right electroacoustic transducer arranged to deliver sound to the right ear canal; and
  a right heart rate sensor arranged at a second position at the right earbud body to provide a right heart rate sensor output, wherein the first position at the left earbud body is different than the second position at the right earbud body; and a right accelerometer sensor to provide a right accelerometer sensor output indicating a right ear direction of motion;

a processor; and a memory comprising computer-executable instructions stored thereon which, when executed by the processor, cause the processor to perform operations comprising:

determining a first wearer heart rate utilizing the left heart rate sensor output;

determining a second wearer heart rate utilizing the right heart rate sensor output;

applying a left weight factor to the first wearer heart rate utilizing the left accelerometer sensor output to generate a weighted first heart rate;

applying a right weight factor to the second wearer heart rate utilizing the right accelerometer sensor output to generate a weighted second heart rate; and determining a composite wearer heart rate utilizing the weighted first heart rate and the weighted second heart rate.

16. The headphones apparatus of claim 15, wherein the left heart rate sensor comprises a first photoplethysmographic sensor and the right heart rate sensor comprises a second photoplethysmographic sensor.

17. The headphones apparatus of claim 15, wherein the first position is located to contact a wearer tragus area or an anti-tragus area and the second position is located to contact a wearer concha area.

* * * * *